United States Patent
Wu et al.

(10) Patent No.: US 8,106,160 B2
(45) Date of Patent: Jan. 31, 2012

(54) N-TERMINAL MODIFIED INTERFERON-ALPHA

(75) Inventors: Bryan T. H. Wu, Taipei (TW);
Tsai-Kuei Shen, Sanchong (TW);
Ming-Pin Hsu, Taipei (TW);
Ching-Leou Teng, San Diego, CA (US)

(73) Assignee: Pharmaessentia Corp., Taipei, Nankang District (TW)

( * ) Notice: Subject to any disclaimer, the term of this patent is extended or adjusted under 35 U.S.C. 154(b) by 333 days.

(21) Appl. No.: 12/243,227

(22) Filed: Oct. 1, 2008

(65) Prior Publication Data

US 2009/0269306 A1    Oct. 29, 2009

Related U.S. Application Data

(60) Provisional application No. 60/976,696, filed on Oct. 1, 2007.

(51) Int. Cl.
*C07K 17/00* (2006.01)
*C07K 14/00* (2006.01)
*C12P 21/04* (2006.01)

(52) U.S. Cl. .................. 530/351; 530/350; 435/69.7

(58) Field of Classification Search .................. None
See application file for complete search history.

(56) References Cited

U.S. PATENT DOCUMENTS

| 5,166,322 A | 11/1992 | Shaw et al. |
| 5,256,769 A * | 10/1993 | Kato et al. .................... 530/351 |
| 5,710,027 A | 1/1998 | Hauptmann et al. |
| 2007/0185135 A1 * | 8/2007 | Wu et al. ....................... 514/256 |
| 2007/0225205 A1 | 9/2007 | Patten et al. |

FOREIGN PATENT DOCUMENTS

| WO | WO 00/09143 | * | 2/2000 |
| WO | WO 01/57217 | | 8/2001 |

OTHER PUBLICATIONS

King et al. "Characterization and properties of a modified human interferon-alpha containing an additional 18 amino acids at the N-terminus" Journal of General Virology; 64:1815-1818 (1983).

* cited by examiner

*Primary Examiner* — Christine J Saoud
*Assistant Examiner* — Jegatheesan Seharaseyon
(74) *Attorney, Agent, or Firm* — Occhiuti Rohlicek & Tsao LLP

(57) ABSTRACT

A method of reducing formation of non-natural disulfide bonds in a mature IFN-α by adding one or more amino acid residues to its N-terminus cystein. Also disclosed herein is the IFN-α thus modified.

2 Claims, 5 Drawing Sheets

GGAAAATTCC CCTCTAGAAT AATTTTGTTT AACTTTAAGA AGGAGATATA CATATGT GTGATCTGCC TCAAACCCAC AGCCTGGGTA GCAGGAGGA
                                                            Met Cys Asp Leu Pro Gln Thr His Ser Leu Gly Ser Arg Arg

CCTTTTAAGG GGAGATCTTA TTAAAACAAA TTGAAATTCT TCCTCTATAT GTATACA CACTAGACGG AGTTTGGGTG TCGGACCCAT CGTCCTCCT
                                                                                                        T hrLeuMet Leu Ala Gln Met Arg Arg Ile Ser Leu Phe Ser Cys Leu Lys Asp Arg His Asp Phe Gly Phe Pro Gln Glu Phe Pro Gly Asn Gln Phe

CTTGATGCTC CTGGCCACAGA TGAGGAGAAT CTCTCTTTTC TCCTGCTTGA AGGACAGACA TGACTTTGGA TTTCCCCAGG AGGAGTTTGG CAACCAGTT
Leu Asp Ala  Leu Ala Thr  Glu Glu Asn Leu Ser Phe  Leu Leu Leu Glu  Gly Gln Thr  *** Leu Trp  Phe Pro Gln  Glu Glu Phe Gly   Gln Pro

GAACTACGAG GACCGTGTCT ACTCCCTCTTA GAGAGAAAAG AGGACGAACT TCCTGTCTGT ACTGAAACCT AAAGGGGTCC TCCTCAAACC GTTGGTCAA

Gln Lys Ala Glu Thr Ile Pro Val Leu His Glu Met Ile Gln Ile Phe Asn Leu Phe Ser Thr Lys Asp Ser Ser Ala Ala Trp Asp Glu Thr Leu

CAAAAGGCTG AAACCATCCC TGTCCTCCAT GAGATGATCC AATCTCTTC AGCAGATCTT CAATCTCTTC TGCTTGGGAT GAGACCCTC

GTTTCCGAC TTTGGTAGGG ACAGGAGTA CTCTACTAGG TCGTCTAGAA GTTAGAGAAG TCGTGTTTCC TGAGTAGACG ACGAACCCTA CTCTGGGAG

LeuAspLys Phe Tyr Thr Glu Leu Tyr Gln Gln LeuAsn Asp Leu Ala Cys Val Ile Gln Gly Val Gly Val Thr Glu Thr ProLeu Met LysGluA

TAGACAAATT CTACACTGAA CTCTACCAGC AGCTGAATGA CCTGGAAGCC TGTGTGATAC AGGGGGTGG GGTGACAGAG ACTCCCCTGA TGAAGGAGG

ATCTGTTTAA GATGTGACTT GAGATGGTCG TCGACTTACT GGACCTTCG ACACACTATG TCCCCCACC CCACTGTCTC TGAGGGGACT ACTTCCTCC spSer Ile Leu Ala Val Arg Lys Tyr Phe Gln Arg Ile Thr Leu Tyr Leu Lys Glu Lys Lys Tyr Ser Pro Cys Ala Trp Glu Val Val Arg Ala Glu Ile

CTCCATTCTG GCTGTGAGGA AATACTTCCA AGAATCACT CTCTATCTGA AAGAGAAGAA ATACAGCCCT TGTGCCTGGG AGTTGTCAG AGCAGAAAT

GAGGTAAGAC CGACACTCCT TTATGAAGGT TCTTAGTGA GAGATAGACT TTCTCTTCTT TATGTCGGGA ACACGGACCC TCCAACAGTC TCGTCTTTA

Met Arg Ser Phe Ser Leu Ser Thr Asn Leu Gln Glu Ser Leu Arg Ser Lys Glu ***

ATGAGATCTT TTTCTTTGTC AACAAACTTG CAAGAAAGTT TAAGAAGTAA GGAATGATAA GGATCCGAAT TCGAGCTCCG TGACAAGCT TGCGGCCGC
                                                                              BamHI      EcoRI
                                                                                                    HindIII
TACTCTAGAA AAAGAAACAG TTGTTTGAAC GTTCTTTCAA ATTCTTCATT CCTTACTATT CCTAGGCTTA AGCTCGAGGC AGCTGTTCGA ACGCCGGCG

CGGGGGCGGG AAAAATTCCC CCTCTAGAAT AATTTTGTTT AACTTTAAGA AGGAGATATA CATATGCCGT GTGATCTGCC TCAAACCCAC AGCCTGGGT
GCCCCCGCCC TTTTTAAGGG GGAGATCTTA TTAAAACAAA TTGAAATTCT TCCTCTATAT GTATACGGCA CACTAGACGG AGTTTGGGTG TCGGACCCA
er Arg Thr Leu Met Leu Ala Gln Met Arg Arg Ile Ser Leu Phe Ser Cys Leu Lys Asp Arg His Asp Phe Gly Phe Pro Gln Glu Glu Phe G

Met Pro Cys Asp Leu Pro Gln Thr His Ser Leu Gly

GCAGGAGGAC CTTGATGCTC CTGGCACAGA TGAGGAGAAT CTCTCTTTTC TCCTGCTTGA AGGACAGACA TGACTTTGGA TTTCCCCAGG AGGAGTTTG
CGTCCTCCTG GAACTACGAG GACCGTGTCT ACTCCTCTTA GAGAGAAAAG AGGACGAACT TCCTGTCTGT ACTGAAACCT AAAGGGGTCC TCCTCAAAC
ly Asn Gln Phe Gln Lys Ala Glu Thr Ile Pro Val Leu His Glu Met Ile Gln Gln Ile Phe Asn Leu Phe Ser Thr Lys Asp Ser Ser Ala Ala Trp Asp

CAACCAGTTC CAAAAGGCTG AAACCATCCC TGTCCTCCAT GAGATGATCC AGCAGATCTT CAATCTCTTC AGCACAAAGG ACTCATCTGC TGCTTGGGA
GTTGGTCAAG GTTTTCCGAC TTTGGTAGGG ACAGGAGTA CTCTACTAGG TCGTCTAGAA GTTAGAGAAG TCGTGTTTCC TGAGTAGACG ACGAACCCT
Glu Thr Leu Leu Asp Phe Tyr Thr Glu Leu Tyr Gln Leu Asn Asp Leu Glu Ala Cys Val Ile Gln Gly Val Gly Val Thr Glu Thr Pro Leu

GAGACCCTCC TAGACAAATT CTACACTGAA CTCTACCAGC AGCTGAATGA CCTGGAAGCC TGTGTGATAC AGGGGGTGGG GGTGACAGAG ACTCCCCTG
CTCTGGGAGG ATCTGTTTAA GATGTGACTT GAGATGGTCG TCGACTTACT GGACCTTCGG ACACACTATG TCCCCCACCC CCACTGTCTC TGAGGGGAC
et Lys Glu Asp Ser Ile Leu Ala Val Arg Lys Tyr Phe Gln Arg Ile Thr Leu Tyr Leu Lys Glu Lys Lys Tyr Ser Pro Cys Ala Trp Glu Val Val A

TGAAGGAGGA CTCCATTCTG GCTGTGAGGA AATACTTCCA AAGAATCACT CTCTATCTGA AAGAGAAGAA ATACAGCCCT TGTGCCTGGG AGGTTGTCA
ACTTCCTCCT GAGGTAAGAC CGACACTCCT TTATGAAGGT TTCTTAGTGA GAGATAGACT TTCTCTTCTT TATGTCGGGA ACACGGACCC TCCAACAGT
rg Ala Glu Ile Met Arg Ser Phe Ser Leu Ser Thr Asn Leu Gln Glu Ser Leu Arg Ser Lys Glu ***

BamHI                         EcoRI                        HindIII
AGCAGAAATC ATGAGAAGCT TTTCTTTGTC AACAAACTTG CAAGAAAGTT TAAGAAGTAA GGAATGATAA GGATCCGAAT TCGAGCTCCG TCGACAAGC
TCGTCTTTAG TACTCTAGA AAAGAAACAG GTTGTTTGAAC GTTCTTTCAA ATTCTTCATT CCTTACTATT CCTAGGCTTA AGCTCGAGGC AGCTGTTCG

N-TERMINAL MODIFIED INTERFERON-ALPHA

CROSS-REFERENCE TO RELATED APPLICATION PARAGRAPH

This application claims the benefit of U.S. Provisional Application No. 60/976,696 filed on Oct. 1, 2007. The contents of which, is hereby incorporated by reference in its entirety

BACKGROUND

Interferons (IFNs), including IFN-α, IFN-β, and IFN-γ, are natural proteins produced by immune cells in response to foreign agents (e.g., pathogens) or abnormal self agents (e.g., cancer cells). They have been widely used in treating viral infection and cancer.

Mature human IFN-α-2b (hIFN-α2b) and its counterparts in other species have two naturally-occurring disulfide bonds, which are crucial to their therapeutic applications. In hIFN-α2b, these two disulfide bonds are formed between $Cys_1$-$Cys_{98}$ and $Cys_{29}$-$Cys_{138}$, respectively. The former is required for the protein activity. Loss of the latter, on the other hand, renders the protein immunogenic.

hIFN-α2b is commonly prepared by expressing its encoding cDNA in *E. coli*. It has been found that the protein thus prepared contains a substantial amount of structural isoforms, including oligomers and slow monomers, both of which migrate slower than their native counterparts in SDS-polyacrymide gel electrophoresis under non-reducing conditions. These isoforms, resulting from formation of non-natural inter- or intra-molecular disulfide bonds, have no therapeutic value as they are either inactive or immunogenic. It is therefore highly desired to develop new techniques for producing IFN-α proteins with little isoform contamination.

SUMMARY

The present invention is based on the unexpected discovery that addition of an amino acid residue to the N-terminus cystein ($Cys_1$) of mature hIFN-α2b reduces formation of non-natural disulfide bonds, thereby substantially lowering the level of its structural isoforms.

In one aspect, this invention features an isolated polypeptide including a first fragment, which has 1-5 (e.g., 1, 2, and 3) amino acid residues, and a second fragment, the N-terminal portion of which is a mature IFN-α having $Cys_1$ (e.g., mature hIFN-α2b). The first fragment is linked to $Cys_1$ of the mature IFN-α via a peptide bond. In one example, the first fragment is a single amino acid, e.g., a proline. Of note, when the first fragment is a single amino acid, it cannot be a methionine. This polypeptide can be used for treating diseases such as viral infection and cancer.

In another aspect, this invention features a nucleic acid including a nucleotide sequence that encodes the polypeptide described above.

Also within the scope of this invention is a method for reducing formation of non-natural disulfide bonds in a mature IFN-α by adding 1-5 amino acid residues to $Cys_1$ of the mature IFN-α. For example, reduced formation of non-natural disulfide bonds in hIFN-α2b is achieved by adding a proline residue to its $Cys_1$.

Other features or advantages of the present invention will be apparent from the following drawings and detailed description of several embodiments, and also from the appending claims.

DESCRIPTION OF DRAWINGS

FIG. 1. shows the amino acid sequence of hIFN-α2b and the its encoding nucleic acid sequence.

FIG. 2. shows the amino acid sequence of a modified mature hIFN-α2b (Pro-IFN-α2b) and its encoding nucleic acid sequence.

DETAILED DESCRIPTION

Figure 3:
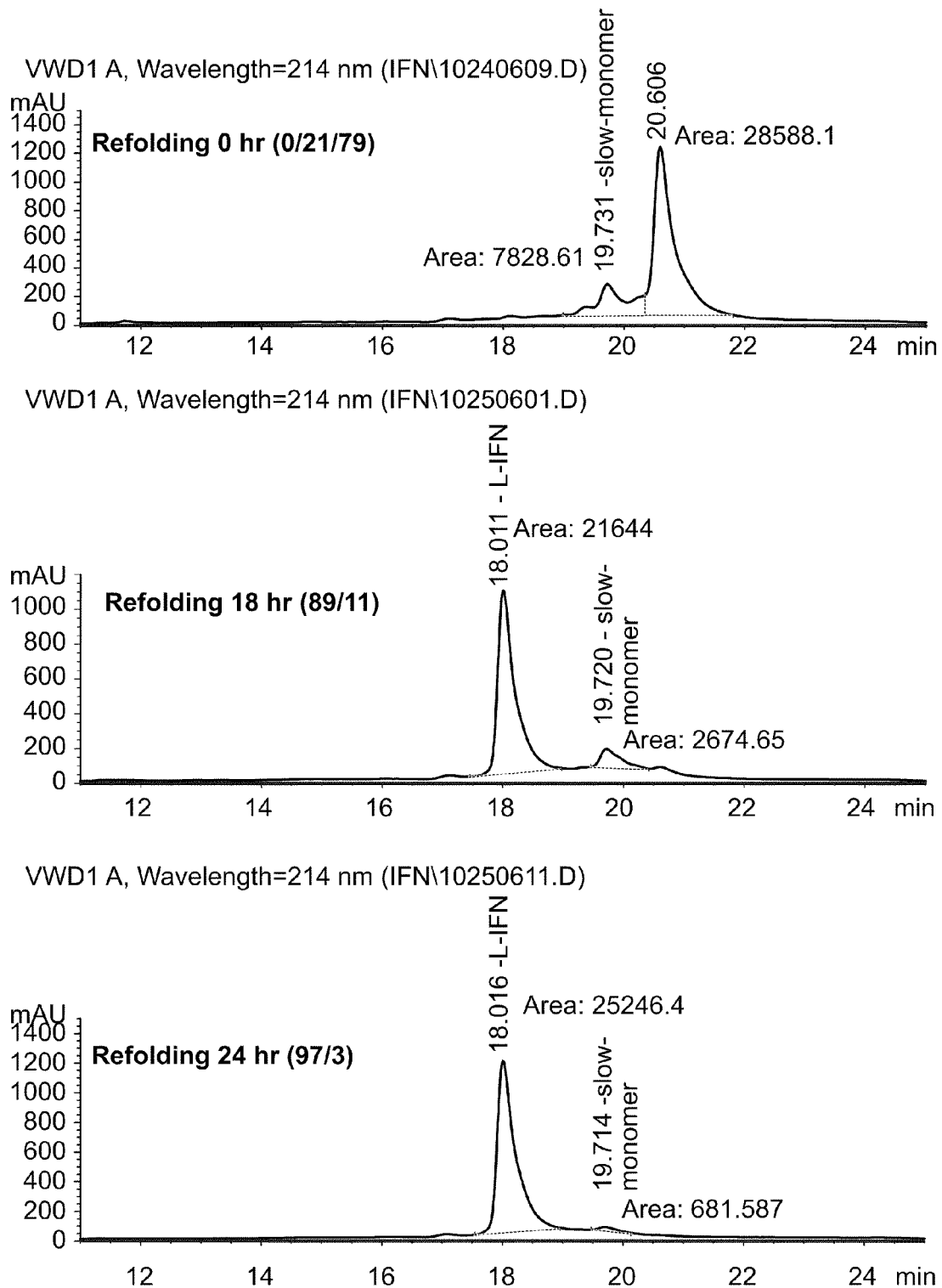
FIG. 3. is a High Performance Liquid Chromatograph ("HPLC") graph showing refolding of mature hIFN-α2b at different time points. Right peak: slow monomers of hIFN-α2b. Left peak: hIFN-α2b in its native form.

The present invention aims at reduction of forming non-natural disulfide bonds in a mature IFN-α, which has been achieved by adding 1-5 amino acid residues to $Cys_1$ of the mature IFN-α.

Accordingly, this invention provides an isolated polypeptide that includes two fragments: the first fragment consisting of up to five amino acid residues and the second fragment including a mature IFN-α at its N-terminal portion. The first fragment is linked to $Cys_1$ of the mature IFN-α through a peptide bond. IFN-α proteins having $Cys_1$ in their mature forms can be identified by searching a protein database, e.g., the GenBank database. Examples of such IFN-α proteins include human IFN-α2b (GenBank Accession No. AAP20099; see also FIG. 1), pig IFN-α (GenBank Accession No. BAE93462), dog IFN-α (GenBank Accession No. BAE92736), and cattle IFN-α (GenBank Accession No. AAP87280).

The first fragment described above can be a single amino acid residue, e.g., a proline. This single amino acid residue, however, cannot be a methionine, as it would be removed in cells. The first fragment can also be a peptide having 2-5 amino acid residues, the sequence of which is inconsequential.

The isolated polypeptide described above can be prepared using recombinant technology. Below is an example. A gene encoding an IFN-α is isolated by methods known in the art. See, e.g., Sambrook et al., *Molecular Cloning: A Laboratory Manual*, $2^{nd}$ Edition, Cold Spring Harbor, N.Y., 1989. This gene is then modified by adding a nucleotide sequence encoding the fragment described above directly to the genetic coden encoding $Cys_1$ of the IFN-α. This modification can be achieved by, e.g., polymerase chain reaction (PCR). The gene thus modified, which encodes the N-terminal modified IFN-α, can then be expressed in *E. coli*, yeast, insect, or mammalian cells.

The isolated polypeptide can also be prepared by synthetic methods or a combination of synthetic and recombinant methods. In one example, the above-described first fragment is added by a synthetic method to the N-terminus of a mature IFN-α that is expressed and purified from host cells.

One can formulate the isolated polypeptide with a pharmaceutically acceptable carrier to produce a pharmaceutical composition. A pharmaceutically acceptable carrier refers to a carrier that is compatible with the active ingredient of the composition (and preferably, capable of stabilizing the active ingredient) and not deleterious to the subject to be treated. Suitable carriers include microcrystalline cellulose, mannitol, glucose, defatted milk powder, polyvinylpyrrolidone, and starch, or a combination thereof. This composition can then be presented in a variety of forms, such as tablet, capsule, powder, or liquid.

The composition containing the isolated polypeptide can be administered to a subject via suitable routes, e.g., intravenous injection or subcutaneous injection, once or multiple times per day or once every several days. A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bio-availability enhancers which are commonly used in the manufacture of pharmaceutically acceptable solid, liquid, or other dosage forms can also be used for the purpose of formulation.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

Example 1

Preparation of Recombinant hIFN-α2b and N-Terminal Modified hIFN-α2b (Pro-hIFN-α2b)

A first nucleic acid encoding hIFN-α2b was amplified by PCR using human genomic DNA as a template. See FIG. 1. The PCR primers were designed based on the flanking sequences of the coding region of the hIFN-α2b gene (GenBank Accession #NM_000605). The PCR product thus obtained was cloned into pGEM-T vector (Promega) and then subcloned into pET-24a (Novagen), a protein expression vector.

A second nucleic acid encoding Pro-hIFN-α2b was obtained by modifying the first nucleic acid described above via PCR amplification using primers designed according to the nucleic acid sequence shown in FIG. 2. Briefly, two additional codens, ATG and CCG (encoding Met and Pro, respectively) were added to the 5' of coden TGT that encodes $Cys_1$ of mature hIFN-α2b. This nucleic acid was also cloned into expression vector pET-24a.

pET-24a vectors, carrying the hIFN-α2b and Pro-hIFN-α2b genes, were then transformed into E. coli BLR-Codon-Plus (DE 3)-RIL strain (Novagene). E. coli clones expressing high levels of these two proteins were selected. As designed, the nascent protein expressed from the Pro-hIFN-α2b gene has a Met at its N-terminus (Met-Pro-Cys-). This Met residue was removed in E. coli via internal enzymatic digestion, resulting in a mature protein having an N-terminal Pro, which is linked to the $Cys_1$ of hIFN-α2b (Pro-Cys-).

The E. coli clone expressing either hIFN-α2b or Pro-hIFN-α2b was cultured in a 1000 ml flask containing 250 ml SYN Broth medium (soytone, yeast extract, and NaCl) with karamycin (50 ug/mL) and chloramphenical (50 ug/mL) at 37° C., 200 rpm for 16 hours. 220 ml of the overnight culture were then transferred to a 5-liter jar fermentator (Bioflo 3000; New Brunswick Scientific Co., Edison, N.J.) containing 3 L define medium (10 g/L glucose, 0.7 g/L $MgSO_4.7H_2O$, 4 g/L $(NH4)_2HPO_4$, 3 g/L $KH_2PO_4$, 6 g/L $K_2HPO_4$, 1.7 g/L citrate, 10 g/L yeast extract, 10 ml/L Trace Element, and 2 g/L isoleucine) with karamycin (25 ug/mL), chloramphenical (25 ug/mL), 0.4% glycerol, and 0.5% (v/v) trace elements (10 g/L of $FeSO_4.7H_2O$, 2.25 g/L of $ZnSO_4.7H_2O$, 1 g/L of $CuSO_4.5H_2O$, 0.5 g/L of $MnSO_4.H2O$, 0.3 g/L of $H_3BO_3$, 2 g/L of $CaCl_2.2H_2O$, 0.1 g/L of $(NH_4)_6Mo_7O_{24}$, 0.84 g/L EDTA, and 50 ml/L HCl). The oxygen concentration in the medium was controlled at 35% and its pH maintained at 7.1 by adding a 37% ammonia water whenever necessary. A feeding solution containing 800 g/L of glucose and 20 g/L of $MgSO_4.7H_2O$ was prepared. When the dissolved oxygen rose to a value greater than the set point, an appropriate volume of the feeding solution was added to increase the glucose concentration in the culture medium. The expression of the hIFN-α2b or the Pro-hIFN-α2b gene was induced by IPTG at a final concentration of 0.7 mM, then addition of feeding material (yeast extract and trace element). E. coli cells expressing these proteins were collected five hours after IPTG induction.

The collected E. coli cells were resuspended in TEN buffer (50 mM Tris-HCl, pH 7.0; 1 mM EDTA, and 100 mM NaCl) in a ratio of 1:10 (wet weight g/mL), disrupted by a homogenizer, and then centrifuged at 10,000 rpm for 20 min. The pellet containing inclusion bodies (IBs) was washed twice with TEN buffer and centrifuged as described above, suspended in a ration of 1 ml solution: 2.5 g pellet wet weight g/mL of a 4 M guanidium HCl (GnHCl) aqueous solution, and then centrifuged at 20,000 rpm for 20 min. The IBs, containing recombinant hIFN-α2b, were then solubilized in 50 mL of 6 M GuHCl with 5 mM DTT, which was then stirred at room temperature for 1.5 hr followed by centrifugation at 20,000 rpm for 20 min at 25° C. The supernatant was collected. In this process, the recombinant hIFN-α2b or Pro-hIFN proteins were denatured.

Example 2

Refolding of hIFN-α2b and Pro-IFN-α2b

The above-described IBs were mixed with 1.5 L freshly prepared refolding buffer (100 mM Tris-HCl (pH 7.0), 0.5 M L-Arginine, 2 mM EDTA). The reaction mixture thus formed was incubated for 24~36 hr without stirring at room temperature to allow refolding of the recombinant hIFN-α2b and Pro-hIFN-α2b proteins. The refolded proteins were then dialyzed against 20 mM Tris-HCl buffer, pH 7.0 and further purified by Q-Sepharose column chromatography described below.

A Q-Sepharose column (GE Healthcare, Pittsburgh, Pa.) was pre-equilibrated and washed with a 20 mM Tris-HCl buffer (pH 7.0). The refolded recombinant proteins were then loaded onto the equilibrated Q-Sepharose column and eluted with a 20 mM Tris-HCl buffer (pH 7.0) containing 80 mM NaCl. Fractions containing Pro-hIFN-α2b were collected based on their absorbance at 280 nm. The concentrations of these proteins were determined by a protein assay kit using the Bradford method (Pierce, Rockford, Ill.).

The conformation of the refolded recombinant proteins was determined using C18 reverse phase HPLC (RP-HPLC), in which native-formed proteins and slow monomers were separated (represented by different peaks shown in FIGS. 3 and 4). The RP-HPLC analysis was conducted on an Angilent HPLC system equipped with an automated gradient controller, two buffer pumps, UV detector, and a recorder-integrator. A C18 HPLC column (46 mm×250 mm, 5 μm particle size; 300 Å pore size) was equilibrated in 80% buffer A: 0.2% (v/v) TFA in 30:70 acetonitrile:water (HPLC grade). The proteins were eluted from the C18 HPLC column using buffer B (0.2% TFA in 80:20 acetonitrile:water) at a flow rate of 1 ml/min according to the following gradient:

| Time (min) | Eluent A | Eluent B |
| --- | --- | --- |
| 0 | 72 | 28 |
| 1 | 72 | 28 |
| 5 | 67 | 33 |
| 20 | 63 | 37 |
| 30 | 57 | 43 |
| 40 | 40 | 60 |
| 42 | 40 | 60 |
| 50 | 72 | 28 |

Figure 4:
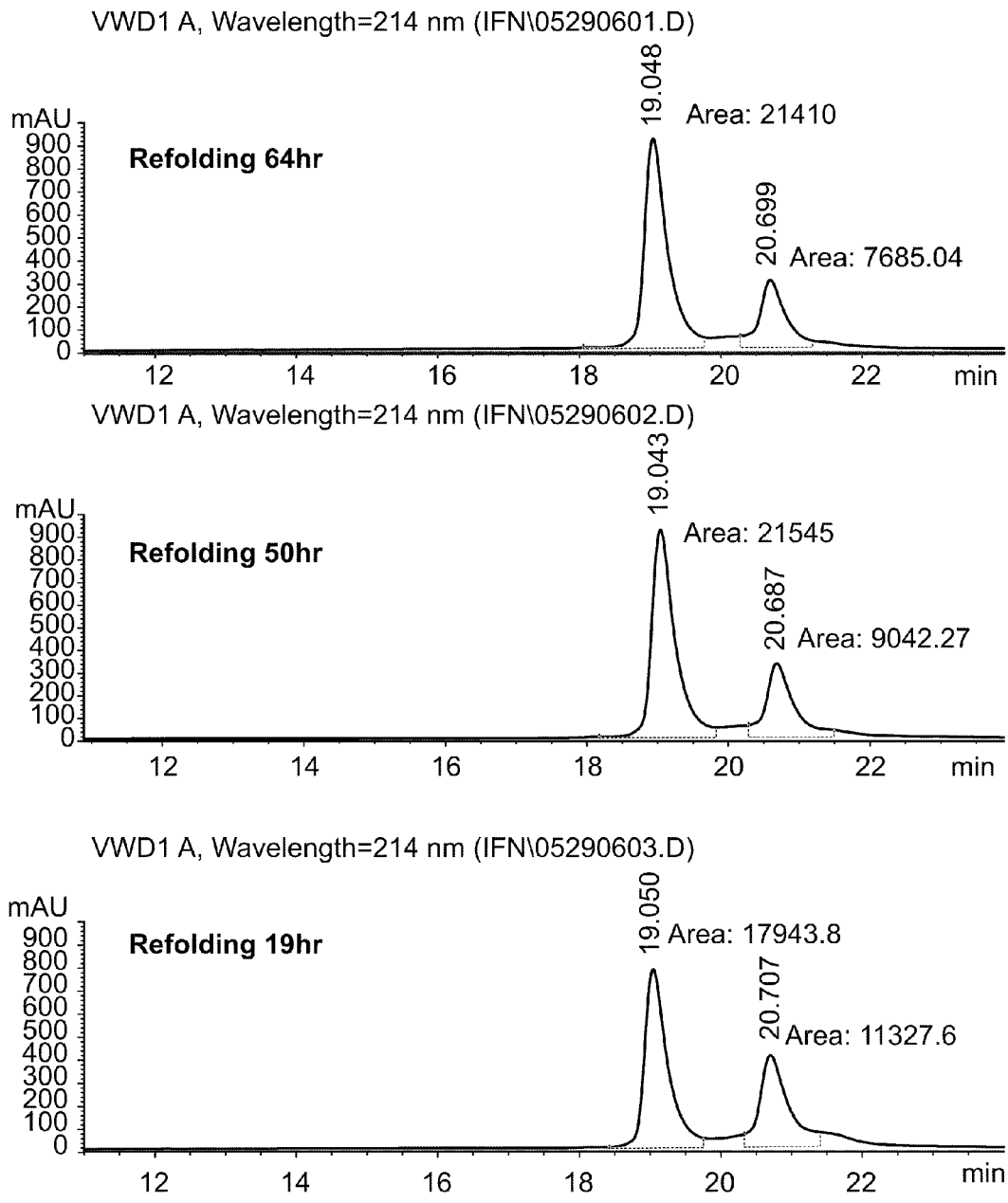
FIG. 4. is an HPLC graph showing refolding of Pro-IFN-α2b at different time points. Peak A: unfolded Pro-IFN-α2b. Peak B: slow monomers of Pro-IFN-α2b. Peak C: Pro-IFN-α2b in its native form.

Results obtained from the C18 HPLC analysis indicate that a substantial amount of the refolded recombinant hIFN-α2b proteins are slow monomers (right peak in FIG. 3). Differently, there is only little contamination of slow monomers in refolded recombinant Pro-hIFN-α2b proteins, see peak B in FIG. 4.

Example 3

Figure 5:
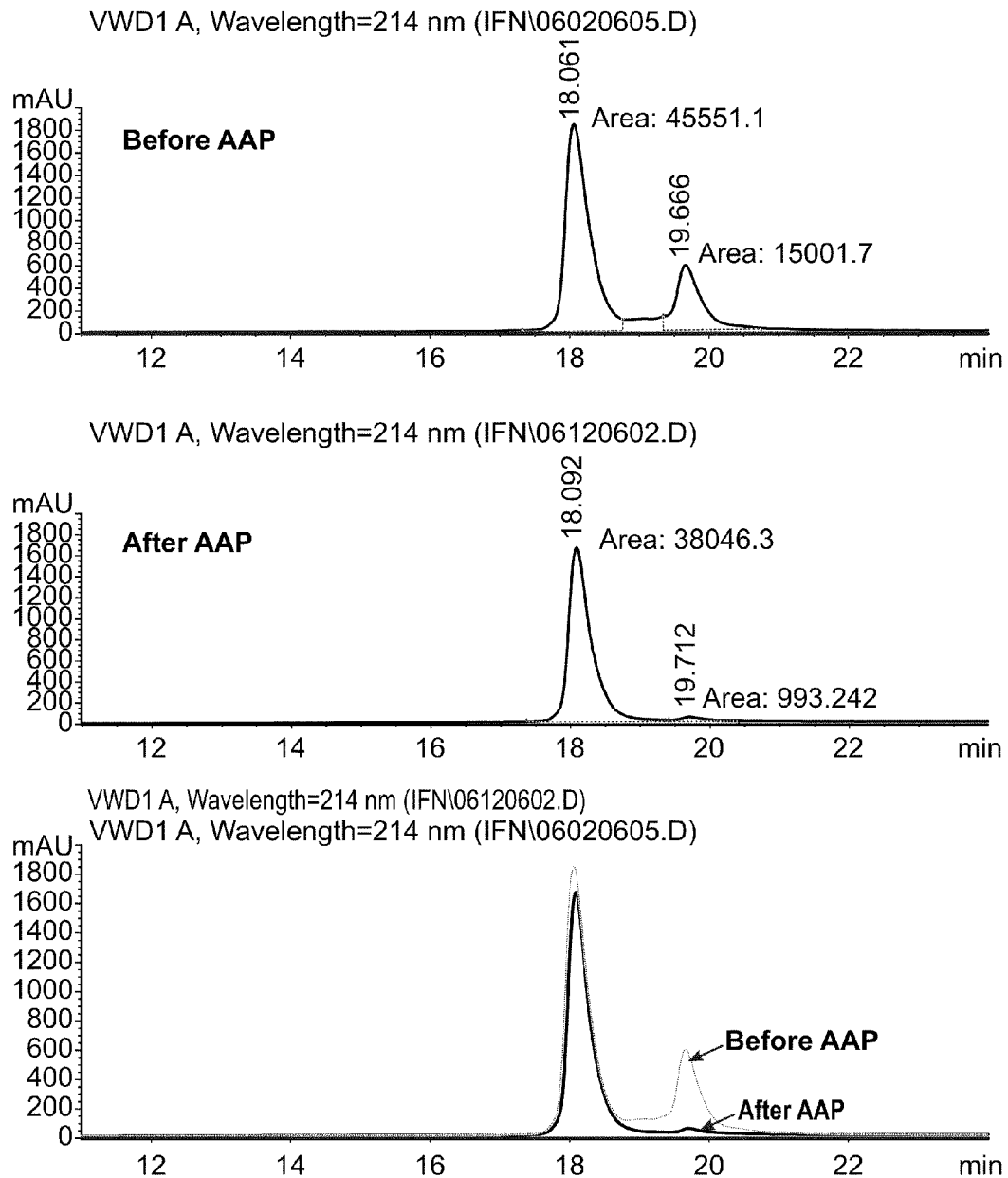
FIG. 5. is an HPLC graph showing native and structural isoforms of hIFN-α2b before and after ammonium sulfate/sodium chloride treatment. Peak A: slow monomers of hIFN-α2b. Peak B: hIFN-α2b in its native form.

Separation of Native hIFN-α2b and hIFN-α2b Isoforms hIFN-α2b was purified by Q-Sepharose column chromatography as described above. hIFN-α2b isoforms, including oligomers and slow monomers, contained in the purified proteins were removed according to the method described in U.S. Pat. No. 4,534,906. Briefly, the proteins were mixed with ASP buffer (3M ammonium sulfate and 1M NaOAc) to the final concentration (0.9 M ammonium sulfate and 20 mM NaOAc) at the pH value of 4.5. The mixture was incubated at room temperature (e.g., 34~40° C.) for 20 minutes to effect formation of protein precipitates, which include slow monomers and oligomers. The precipitates were removed by centrifugation and the supernatant containing hIFN-α2b in native form was collected. The proteins samples before and after ammonium sulfate/sodium chloride treatment were analyzed in C18 reverse phase HPLC and the results thus obtained were shown in FIG. 5. hIFN-α2b proteins prepared by Q-Sepharose column purification include a substantial amount of isoforms. See the right peak in the top panel of FIG. 5. These isoforms have been removed after ammonium sulfate/sodium chloride treatment.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. An isolated polypeptide comprising a Pro and a mature interferon alpha that has an N-terminal Cys, wherein the Cys is linked to the Pro via a peptide bond.

2. The polypeptide of claim 1, wherein the interferon alpha is human interferon alpha-2b.

* * * * *

SEQUENCE LISTING

<160> NUMBER OF SEQ ID NOS: 4

<210> SEQ ID NO 1
<211> LENGTH: 595
<212> TYPE: DNA
<213> ORGANISM: Homo sapiens
<220> FEATURE:
<221> NAME/KEY: CDS
<222> LOCATION: (54)..(551)

<400> SEQUENCE: 1

```
ggaaaattcc cctctagaat aattttgttt aactttaaga aggagatata cat atg      56
                                                             Met
                                                             1 tgt gat ctg cct caa acc cac agc ctg ggt agc agg agg acc ttg atg   104
Cys Asp Leu Pro Gln Thr His Ser Leu Gly Ser Arg Arg Thr Leu Met
        5                  10                  15 ctc ctg gca cag atg agg aga atc tct ctt ttc tcc tgc ttg aag gac   152
Leu Leu Ala Gln Met Arg Arg Ile Ser Leu Phe Ser Cys Leu Lys Asp
            20                  25                  30 aga cat gac ttt gga ttt ccc cag gag gag ttt ggc aac cag ttc caa   200
Arg His Asp Phe Gly Phe Pro Gln Glu Glu Phe Gly Asn Gln Phe Gln
        35                  40                  45 aag gct gaa acc atc cct gtc ctc cat gag atg atc cag cag atc ttc   248
Lys Ala Glu Thr Ile Pro Val Leu His Glu Met Ile Gln Gln Ile Phe
    50                  55                  60                  65 aat ctc ttc agc aca aag gac tca tct gct gct tgg gat gag acc ctc   296
Asn Leu Phe Ser Thr Lys Asp Ser Ser Ala Ala Trp Asp Glu Thr Leu
```

```
                      70                  75                  80
cta gac aaa ttc tac act gaa ctc tac cag cag ctg aat gac ctg gaa        344
Leu Asp Lys Phe Tyr Thr Glu Leu Tyr Gln Gln Leu Asn Asp Leu Glu
                85                  90                  95 gcc tgt gtg ata cag ggg gtg ggg gtg aca gag act ccc ctg atg aag        392
Ala Cys Val Ile Gln Gly Val Gly Val Thr Glu Thr Pro Leu Met Lys
            100                 105                 110 gag gac tcc att ctg gct gtg agg aaa tac ttc caa aga atc act ctc        440
Glu Asp Ser Ile Leu Ala Val Arg Lys Tyr Phe Gln Arg Ile Thr Leu
        115                 120                 125 tat ctg aaa gag aag aaa tac agc cct tgt gcc tgg gag gtt gtc aga        488
Tyr Leu Lys Glu Lys Lys Tyr Ser Pro Cys Ala Trp Glu Val Val Arg
130                 135                 140                 145 gca gaa atc atg aga tct ttt tct ttg tca aca aac ttg caa gaa agt        536
Ala Glu Ile Met Arg Ser Phe Ser Leu Ser Thr Asn Leu Gln Glu Ser
                150                 155                 160 tta aga agt aag gaa tgataaggat ccgaattcga gctccgtcga caagcttgcg        591
Leu Arg Ser Lys Glu
                165 gccg                                                                   595

<210> SEQ ID NO 2
<211> LENGTH: 166
<212> TYPE: PRT
<213> ORGANISM: Homo sapiens

<400> SEQUENCE: 2

Met Cys Asp Leu Pro Gln Thr His Ser Leu Gly Ser Arg Arg Thr Leu
1               5                   10                  15

Met Leu Leu Ala Gln Met Arg Arg Ile Ser Leu Phe Ser Cys Leu Lys
            20                  25                  30

Asp Arg His Asp Phe Gly Phe Pro Gln Glu Glu Phe Gly Asn Gln Phe
        35                  40                  45

Gln Lys Ala Glu Thr Ile Pro Val Leu His Glu Met Ile Gln Gln Ile
    50                  55                  60

Phe Asn Leu Phe Ser Thr Lys Asp Ser Ser Ala Ala Trp Asp Glu Thr
65                  70                  75                  80

Leu Leu Asp Lys Phe Tyr Thr Glu Leu Tyr Gln Gln Leu Asn Asp Leu
                85                  90                  95

Glu Ala Cys Val Ile Gln Gly Val Gly Val Thr Glu Thr Pro Leu Met
            100                 105                 110

Lys Glu Asp Ser Ile Leu Ala Val Arg Lys Tyr Phe Gln Arg Ile Thr
        115                 120                 125

Leu Tyr Leu Lys Glu Lys Lys Tyr Ser Pro Cys Ala Trp Glu Val Val
130                 135                 140

Arg Ala Glu Ile Met Arg Ser Phe Ser Leu Ser Thr Asn Leu Gln Glu
145                 150                 155                 160

Ser Leu Arg Ser Lys Glu
                165

<210> SEQ ID NO 3
<211> LENGTH: 598
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (64)..(564)
```

<400> SEQUENCE: 3

```
cgggggcggg aaaaattccc cctctagaat aattttgttt aactttaaga aggagatata      60 cat atg ccg tgt gat ctg cct caa acc cac agc ctg ggt agc agg agg     108
    Met Pro Cys Asp Leu Pro Gln Thr His Ser Leu Gly Ser Arg Arg
    1               5                   10                  15 acc ttg atg ctc ctg gca cag atg agg aga atc tct ctt ttc tcc tgc     156
Thr Leu Met Leu Leu Ala Gln Met Arg Arg Ile Ser Leu Phe Ser Cys
            20                  25                  30 ttg aag gac aga cat gac ttt gga ttt ccc cag gag gag ttt ggc aac     204
Leu Lys Asp Arg His Asp Phe Gly Phe Pro Gln Glu Glu Phe Gly Asn
        35                  40                  45 cag ttc caa aag gct gaa acc atc cct gtc ctc cat gag atg atc cag     252
Gln Phe Gln Lys Ala Glu Thr Ile Pro Val Leu His Glu Met Ile Gln
    50                  55                  60 cag atc ttc aat ctc ttc agc aca aag gac tca tct gct gct tgg gat     300
Gln Ile Phe Asn Leu Phe Ser Thr Lys Asp Ser Ser Ala Ala Trp Asp
65                  70                  75 gag acc ctc cta gac aaa ttc tac act gaa ctc tac cag cag ctg aat     348
Glu Thr Leu Leu Asp Lys Phe Tyr Thr Glu Leu Tyr Gln Gln Leu Asn
80                  85                  90                  95 gac ctg gaa gcc tgt gtg ata cag ggg gtg ggg gtg aca gag act ccc     396
Asp Leu Glu Ala Cys Val Ile Gln Gly Val Gly Val Thr Glu Thr Pro
                100                 105                 110 ctg atg aag gag gac tcc att ctg gct gtg agg aaa tac ttc caa aga     444
Leu Met Lys Glu Asp Ser Ile Leu Ala Val Arg Lys Tyr Phe Gln Arg
            115                 120                 125 atc act ctc tat ctg aaa gag aag aaa tac agc cct tgt gcc tgg gag     492
Ile Thr Leu Tyr Leu Lys Glu Lys Lys Tyr Ser Pro Cys Ala Trp Glu
        130                 135                 140 gtt gtc aga gca gaa atc atg aga tct ttt tct ttg tca aca aac ttg     540
Val Val Arg Ala Glu Ile Met Arg Ser Phe Ser Leu Ser Thr Asn Leu
    145                 150                 155 caa gaa agt tta aga agt aag gaa tgataaggat ccgaattcga gctccgtcga     594
Gln Glu Ser Leu Arg Ser Lys Glu
160                 165 caag                                                                 598
```

<210> SEQ ID NO 4
<211> LENGTH: 167
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Met Pro Cys Asp Leu Pro Gln Thr His Ser Leu Gly Ser Arg Arg Thr
1               5                   10                  15

Leu Met Leu Leu Ala Gln Met Arg Arg Ile Ser Leu Phe Ser Cys Leu
            20                  25                  30

Lys Asp Arg His Asp Phe Gly Phe Pro Gln Glu Glu Phe Gly Asn Gln
        35                  40                  45

Phe Gln Lys Ala Glu Thr Ile Pro Val Leu His Glu Met Ile Gln Gln
    50                  55                  60

Ile Phe Asn Leu Phe Ser Thr Lys Asp Ser Ser Ala Ala Trp Asp Glu
65                  70                  75                  80

Thr Leu Leu Asp Lys Phe Tyr Thr Glu Leu Tyr Gln Gln Leu Asn Asp
                85                  90                  95
```

-continued

```
Leu Glu Ala Cys Val Ile Gln Gly Val Gly Val Thr Glu Thr Pro Leu
            100                 105                 110

Met Lys Glu Asp Ser Ile Leu Ala Val Arg Lys Tyr Phe Gln Arg Ile
            115                 120                 125

Thr Leu Tyr Leu Lys Glu Lys Lys Tyr Ser Pro Cys Ala Trp Glu Val
        130                 135                 140

Val Arg Ala Glu Ile Met Arg Ser Phe Ser Leu Ser Thr Asn Leu Gln
145                 150                 155                 160

Glu Ser Leu Arg Ser Lys Glu
                165
```